(12) United States Patent
Eckerbom et al.

(10) Patent No.: US 10,952,641 B2
(45) Date of Patent: Mar. 23, 2021

(54) GAS SAMPLING LINE

(71) Applicant: Masimo Corporation, Irvine, CA (US)

(72) Inventors: Anders Eckerbom, Vaxholm (SE); Robert Zyzanski, Stockholm (SE)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/832,658

(22) Filed: Dec. 5, 2017

(65) Prior Publication Data
US 2018/0153442 A1 Jun. 7, 2018

Related U.S. Application Data

(63) Continuation of application No. 13/063,648, filed as application No. PCT/SE2009/051012 on Sep. 11, 2009, now Pat. No. 9,861,298.

(30) Foreign Application Priority Data

Sep. 15, 2008 (SE) .................................... 0801967-1

(51) Int. Cl.
A61B 5/097 (2006.01)
A61B 5/08 (2006.01)

(52) U.S. Cl.
CPC .............. A61B 5/097 (2013.01); A61B 5/082 (2013.01)

(58) Field of Classification Search
CPC ..................................... A61B 5/097
See application file for complete search history.

(56) References Cited

U.S. PATENT DOCUMENTS

| | | |
|---|---|---|
| 4,705,543 A | 11/1987 | Kertzman |
| 4,960,128 A | 10/1990 | Gordon et al. |
| 4,964,408 A | 10/1990 | Hink et al. |
| 5,042,500 A | 8/1991 | Norlien et al. |
| 5,319,355 A | 6/1994 | Russek |

(Continued)

FOREIGN PATENT DOCUMENTS

| | | |
|---|---|---|
| GB | 2175208 A | 11/1986 |
| WO | WO 98/46277 | 10/1998 |

(Continued)

OTHER PUBLICATIONS

Sijbesma et al., Flue gas dehydration using polymer membranes, Journal of Membrane Science 313, 2008, pp. 263-276 (Year: 2008).*

(Continued)

Primary Examiner — Puya Agahi
(74) Attorney, Agent, or Firm — Knobbe, Martens, Olson & Bear, LLP

(57) ABSTRACT

A gas sampling line having a channel for conducting respiratory gases from a patient respiratory interface to a gas monitor, the gas sampling line comprising, i.a., a gas sampling tube comprised of a polyether block amide material, the polyether segments of which comprise polyethyleneoxide. Use of a tube comprised of a polyether block amide material, the polyether segments of which comprise polyethyleneoxide, for sampling of respiratory gases; and a method for sampling of respiratory gases, the method comprising conducting respiratory gases through such a tube. A gas analysis system for analysing respiratory gases, comprising a gas sampling line as defined above and a gas monitor connectable to the gas sampling line.

18 Claims, 1 Drawing Sheet

(56) References Cited

U.S. PATENT DOCUMENTS

| | | |
|---|---|---|
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,694,922 A * | 12/1997 | Palmer .............. A61M 16/0463 128/202.27 |
| 5,703,161 A | 12/1997 | Steenblock et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,779,522 B2 | 8/2004 | Smith et al. |
| 6,783,573 B2 | 8/2004 | Richardson |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,228,878 B2 * | 6/2007 | Chen .................. A61L 29/04 138/137 |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |

(56) References Cited

U.S. PATENT DOCUMENTS

| | | |
|---|---|---|
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |

(56) References Cited

U.S. PATENT DOCUMENTS

| | | |
|---|---|---|
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0077606 A1* | 6/2002 | Trotta .................. A61L 29/049 604/264 |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0191405 A1 | 10/2003 | Rich et al. |
| 2003/0212312 A1 | 11/2003 | Coffin, IV et al. |
| 2004/0029467 A1 | 2/2004 | Lacroix |
| 2004/0106163 A1 | 6/2004 | Workman, Jr. et al. |
| 2005/0055276 A1 | 3/2005 | Kiani et al. |
| 2005/0161042 A1 | 7/2005 | Fudge et al. |
| 2005/0234317 A1 | 10/2005 | Kiani |
| 2006/0014059 A1 | 1/2006 | Wood |
| 2006/0073719 A1 | 4/2006 | Kiani |
| 2006/0086254 A1* | 4/2006 | Fudge .................... A61B 5/097 96/413 |
| 2006/0189871 A1 | 8/2006 | Al-Ali et al. |
| 2006/0200110 A1* | 9/2006 | Lentz ..................... A61L 29/06 604/524 |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0034964 A1 | 2/2008 | Schmidt et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0174239 A1 | 7/2010 | Yodfat et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tani et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2011/0237969 A1 | 9/2011 | Eckerbom et al. |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0367173 A1 | 12/2016 | Dalvi et al. |
| 2017/0024748 A1 | 1/2017 | Haider |

(56) References Cited

U.S. PATENT DOCUMENTS

| | | |
|---|---|---|
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |

FOREIGN PATENT DOCUMENTS

| | | |
|---|---|---|
| WO | WO 2005/072297 | 5/2005 |
| WO | WO 2006/120683 | 11/2006 |
| WO | WO 2010/030226 A1 | 3/2010 |

OTHER PUBLICATIONS

Barrer, Source: http://en.wikipedia.org/wiki/Barrer?oldid=646860514. Contributors: Calair, Wtmitchell, MZMcBride, Retired username, SmackBot, Bluebot, Due Freq, Flscholten, ydebot, Zginder, MarchBot, Leyo, Reedy Bot, Keepday, Steven J. Anderson, MacIgwnbot, Addbot, Colapeninsula, Barrercorrector and Anonymous: 10. As printed on Jun. 2, 2015.
European Patent Office Third Party Observations, dated Sep. 28, 2012; Appln. No. 09813309.3-2319 / 2326246 PCT/SE2009051012.
Flyer; "Our Materials Science Meets Your Medical Applications", Arkema 2009; 6 pages.
International Search Report: PCT/SE2009/051012; dated Dec. 21, 2009.
Pebax®, Applications Areas, Arkema, Jun. 2000, 11 pages.
Pebax®, Breathable Film, Arkema, Jun. 2007, 2 pages.
Pebax®, In Medical Applications, Arkema, Jun. 2007, 2 pages.
Pebax®, Product Range Overview, Arkema, Jun. 2007, 2 pages.
Sridhar et al., "Development of Crosslinked Polyether-block-amide membrane for CO2/CH4 Separation," 2007, pp. 267-274.
Supplementary European Search Report completed Nov. 30, 2012; Appln. No. EP 09 81 3309.
V.I. Bondar, et al; "Gas Sorption and Characterization of Poly(ether-b-amide) Segmented Block Copolymers", Journal of Polymer Science: Part B: Polymer Physics, vol. 37, pp. 2463-2475, Apr. 26, 1999.
Wikipedia.org: PEBA and PEG.
Yuri Yampolskii, et al; "Membrane Gas Separation", John Wiley & Sons, Ltd, 2010; pp. 257, 263.
Moilanen, et al., Water Dynamics and Proton Transfer in Nafion Fuel Cell Membranes, Langmuir 2008, 24(8), 3690-3698. Published Apr. 15, 2008.
Y. Yampolskii, B. Freeman, "Membrane Gas Separation", John Wiley & Sons, Ltd., 2010, pp. 257-263.
Marcq, J. et al., "Abatement of CO2 Emissions by Means of Membranes—Characterization of Industrial PEBAX™ Films", Environment Protection Engineering, 2005, vol. 31 (3-4), pp. 13-22.
European Patent Office Third Party Observations dated Jun. 8, 2015, Application No. 09813309.3, Patent No. 2326246, WO 2010/030226.
Petition for Inter Parties Review of U.S. Pat. No. 9,861,298 dated Sep. 6, 2019.
U.S. Pat. No. 9,861,298, Eckerbom et al., Issued Jan. 9, 2018 (Exhibit 1001).
Declaration of Petitioner's Expert, Zane Frund, Ph.D., dated Sep. 6, 2019 (Exhibit 1002).
U.S. Pat. No. 95,042,500, Norlien et al., Issued Aug. 27, 1991 (Exhibit 1003).
Sijbesma et al., Flue Gas Dehydration Using Polymer Membranes, J. Membrane Sci 313 (2008) p. 263-276 (Exhibit 1004).
US Publication 2005/0171496, Guldfeldt et al., Published Aug. 4, 2005 (Exhibit 1005).
U.S. Pat. No. 8,053,030, Gilman, Issued Nov. 8, 2011 (Exhibit 1006).
Nguyen, et al., Pervaporation, a Novel Technique for the Measurement of Vapor Transmission Rate of Highly Permeable Films, Polymer Testing 29 (2001) p. 901-911 (Exhibit 1007).
US Publication 2009/0088656, Levitsky et al., Published Apr. 2, 2009 (Exhibit 1008).
Prosecution History of U.S. Pat. No. 9,861,298, patent issued on Jan. 9, 2018 (Exhibit 1009).
USPTO, Decision on Appeal 2016-006238, Exhibit 1010, filed on Sep. 6, 2019 in IPR2019-01583 dated Sep. 18, 2017 (Exhibit 1010).
Arkema Brochure, in Medical Applications—Advantage of Using Pebax (publication date not provided) (Exhibit 1011).
U.S. Pat. No. 6,783,573, Richardson, Issued Aug. 31, 2004 (Exhibit 1012).
Credit Suisse, Report on PEEK Pricing, dated May 13, 2015 (Exhibit 1013).
740SELECT Capnography: Covidien Microstream MicroPod Brochure (publication date not provided) (Exhibit 1014).
Ma et al., Carbon Dioxide Permeability of Proton Exchange Membranes for Fuel Cells, Solid State Ionics 176 (2005) p. 2923-2927 (Exhibit 1015).
Sridhar et al., Development of Crosslinked Poly(ether-block-amide) Membrane for Co2/CH4 Separation, Colloids and Surfaces A: Physicochem, Eng. Aspects 297 (2007) p. 267-274 (Exhibit 1016).
Jansen, Nanotubes Vapour Removal, Attentie, Periodiek der S.V.A. T. Astante, Oct. 2007 (Exhibit 1017).
Portion of File History of European Application No. 098133093.-1660, Jun. 8, 2015 (Exhibit 1018).
Second Portion of File History of European Application No. 098133093.-1660, Jun. 8, 2015 (Exhibit 1019).
Third Portion of File History of European Application No. 098133093.-1660, Jun. 8, 2015 (Exhibit 1020).
Freeman et al., Gas and Liquid Separations Using Membranes: An Overview, 2004 American Chemical Society (Exhibit 1021).
Petitioner's Opening Appeal Brief, dated Nov. 30, 2015 (Exhibit 1022).
Examiners Answer Brief, dated Mar. 28, 2016 (Exhibit 1023).
Petitioner's Reply Brief to Examiner's Answer, dated Jun. 6, 2016 (Exhibit 1024).
E. Peled et al., A Direct Methanol Fuel Cell Based on a Novel Low-Cost Nanoporous Proton-Conducting Membrane, dated Jun. 26, 2000 (Exhibit 1025).

(56) References Cited

OTHER PUBLICATIONS

PEBAX Invioce, dated Jul. 18, 2019 (Exhibit 1026).
Corrected Petition for Inter Parties Review of U.S. Pat. No. 9,861,298 dated Sep. 6, 2019.
Patent Owner Submission of Mandatory Notice Information Pursuant to 37 C.F.R. 42.8(a) dated Sep. 27, 2019.
Patent Owner Preliminary Response dated Dec. 19, 2019.
Decision Granting Institution of Inter Partes Review date Mar. 16, 2019.
File History, U.S. Appl. No. 13/063,648 [Exhibit 2001].
Declaration of Len Czuba [Exhibit 2002].
Curriculum Vitae, Len Czuba [Exhibit 2003].
U.S. Pat. No. 6,783,573, Richardson, Issued Aug. 31, 2004 [Exhibit 2004] [Exhibit 2014].
International Publication No. WO 2005/072297, RIC Investments, LLC, published Aug. 11, 2005 [Exhibit 2005] [Exhibit 2015].
U.S. Pat. No. 6,779,522, Smith et al., Issued Aug. 24, 2004 [Exhibit 2006].
Perma Pure LLC, Frequently Asked Questions, https://web.archive.org/web/20060324193926/http:/www.permapure.com/FAQs.htm [Exhibit 2007].
Perma Pure, LLC, Frequently Asked Questions, https://www.permapure.com/support/faqs/ [Exhibit 2008].
Španěl, P., et al., "On-line measurement of the absolute humidity of air, breath and liquid headspace samples by selected ion flow tube mass spectrometry," Rapid Communications in Mass Spectrometry, 15 (2001). [Exhibit 2009].
Excerpts from Mulder, Marcel, Basic Principles of Membrane Technology, 1996 (2nd ed.) [Exhibit 2010].
Potreck, J., et al., "Mixed Water Vapor/Gas Transport Through the rubbery polymer PEBAX® 1074," Jounral of Membrane Science, 338 (2009). [Exhibit 2011].
Perma Pure, LLC, Press Release, "Fluid Technology Division—Keeping Water Vapor From Breath Gas Analyzers," Feb. 18, 2005. [Exhibit 2012].
Shamu, A., et al., "Mass transfer studies on the dehydration of supercritical carbon dioxide using dense polymeric membranes," Separation and Purification Technology, 209 (2019). [Exhibit 2013].
U.S. Pat. No. 6,783,573, Richardson, Issued Aug. 31, 2004 [Exhibit 2014].
International Publication No. WO5/072297, RIC Investments, LLC, published Aug. 11, 2005 [ [Exhibit 2015].
US Publication No. 2003/0191405, Rich et al., Issued Oct. 9, 2003 [Exhibit 2016].
Declaration of Craig Sunada in *Perma Pure, LLC* V. *Masimo Corporation* dated Aug. 24, 2020 in 20 pages. [Exhibit 1028].
Desposition of Lenoard F. Czuba in *Perma Pure, LLC* V. *Masimo Corporation* dated Aug. 13, 2020 in 113 pages. [Exhibit 1027].

* cited by examiner

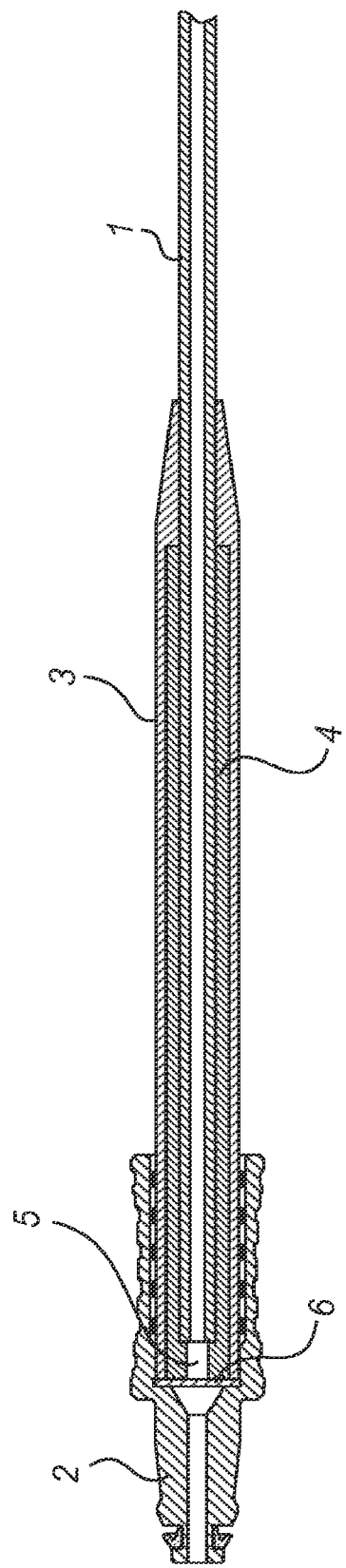

GAS SAMPLING LINE

TECHNICAL FIELD

The present invention relates to a gas sampling line having a channel for conducting respiratory gases from a patient respiratory interface to a gas monitor, and to a gas analysis system comprising such a gas sampling line. Furthermore, the invention relates to the use of a tube for sampling of respiratory gases, and to a method for sampling of respiratory gases.

BACKGROUND ART

In respiratory care, it is often desirable to analyse and monitor the gas composition of a patient's exhaled and/or inhaled breathing gases. For instance, measurement of respiratory $CO_2$, $O_2$, $N_2O$ and anesthetic agents, such as halothane, isoflurane, enflurane, sevoflurane or desflurane, is useful in the care of critically ill patients undergoing anesthesia or mechanical ventilation. Typically, the gas concentrations of the patient's breathing gases are monitored by transferring a portion of the breathing gases through a sampling line to a suitable gas sensor or gas monitor.

The patient's exhaled breathing gases are usually saturated with moisture at body temperature. Thus, water naturally condenses when the gas sample is cooled to room temperature when passed through the sampling line. Collected condensate, together with secretion, bacteria or other contaminants possibly present in the breathing gases, may result in inaccurate readings at the sensor or even adversely affect a delicate gas monitor.

The accuracy of the gas concentrations obtained from a respiratory gas monitor also depends on the ability of the analyser system to direct the gas sample from the patient, through the tube of a sampling line to the gas sensor, without distorting the gas sample flow. One cause of distortion of the gas sample flow may be the adsorption on and/or absorption in the tube material of one of more of the components of the gas sample. Additionally, any physical obstacles in the gas sample line, such as valves or material seams, may distort the gas sample flow. Distortion of the gas sample flow, regardless of cause, can degrade rise time of the measured waveform making accurate analysis, especially at higher breath rates, difficult or impossible.

In order to protect a respiratory gas monitor from water and other contaminants, prior art gas sampling systems employs various means to separate liquids, bacteria etc. from the gas sample flow. It has for instance been known to include in the sampling line a water trap or another moisture separation means between the patient and the gas sensor. The challenge, however, is to design such a water trap or moisture separation means that achieves sufficient efficiency and capacity without distorting the gas sample flow.

U.S. Pat. No. 6,783,573 is directed to a gas sampling system for conducting respiratory gases. A gas sampling tube is configured to conduct the respiratory gases from a patient to a gas monitoring device. An output connector couples the gas sampling tube to the monitor. An output dryer tube is coupled between the gas sampling tube and the output connector. The output dryer tube is characterized by a tube length and a relative moisture removal efficiency. The relative moisture removal efficiency is dependent on the tube length. The tube length is selected to limit the moisture content of the respiratory gases being directed into the respiratory gas monitor to a predetermined level. The output dryer tube may be comprised of Nafion® or may be implemented using microporous filters or molecular sieves. An optional input dryer may be implemented using the same materials used to implement the output dryer.

WO 2005/072297 is directed to a liquid absorbing filter assembly and system using the same. It is disclosed a filter assembly for use in a sidestream gas sampling assembly. The filter assembly includes a hydrophilic liner lining the inner perimeter of a housing for wicking moisture from the gases to be monitored prior to the gases reaching a sensing mechanism. It is contemplated that the housing can be formed from an absorbent material or a gas drying material, such as Nafion®.

However, there is a need for improvement of prior art solutions for respiratory gas analysis in respect of, e.g., low distortion, long lasting moisture and/or water removal, or low cost.

SUMMARY OF THE INVENTION

An object of the present invention is to provide means for sampling of respiratory gases from a patient while protecting a gas monitor from moisture and/or water as well as providing a reading of high accuracy of gas components, including air gases, such as $CO_2$, $N_2O$ and anesthetic agents. Thus, it is an object of the invention to allow for a signal having a low distortion, particularly in a low flow gas sample and/or a gas sample from a patient having a high breath rate.

Another object of the present invention is to provide means for sampling of respiratory gases from a patient without employment of a conventional water trap. It is thus an object of the invention to provide a simple and cheap solution in comparison to conventional means comprising such water trap as well as to provide prolonged operating times in comparison to those of conventional means.

A further object of the present invention is to provide means of low material and production cost fulfilling the mentioned aspects of moisture and/or water removal as well as accurate gas component reading.

Another object of the present invention is to improve sidestream measurements of respiratory gases, i.e. when in order to influence a patient as little as possible a small fraction only of the inhaled and/or exhaled respiratory gas is diverted for measurement from the main flow of respiratory gas between a patient and, e.g. a breather apparatus.

Other objects or advantages of the invention should be apparent to a person skilled in the art after having read the description below.

In a first aspect of the invention, there is provided a gas sampling line having a channel for conducting respiratory gases from a patient respiratory interface to a gas monitor, the gas sampling line comprising a patient respiratory interface connector adapted to couple the gas sampling line to a patient respiratory interface;

a gas sampling tube adapted to conduct respiratory gases; and a gas monitor connector adapted to couple the gas sampling line to a gas monitor, wherein the gas sampling tube is comprised of a polyether block amide material, the polyether segments of which comprise polyethyleneoxide.

Thus, it has been surprisingly found that when passing a sample of respiratory gases through a gas sampling tube comprised of a polyether block amide material, the polyether segments of which comprise polyethyleneoxide, moisture and condensed water present in the gas sample permeate through the tube material to provide a dried gas sample, while components (such as $CO_2$ or anesthetic agents) of the gas sample passes the tube portion essentially undistorted (i.e. without being absorbed in or adsorbed to the tube material) to allow for an accurate reading at the gas monitor.

Polyether block amides (PEBAs) are thermoplastic elastomers well adapted for applications such as molded or extruded articles, films etc. They are block copolymers obtained by polycondensation of a carboxylic acid polyamide with an alcohol termination polyether. A polyether block amide elastomer consists of a regular linear chain of rigid polyamide segments and flexible polyether segments having the following general formula $$HO-[CO-A-CO-O-B-O]_n-H$$

where A represents the polyamide segment and B represent the polyether segment. Polyamide is a polymer comprising the characteristic amide group $$-NH-CO-$$

in the repeating units of the polymer chain. In the present invention, the polyether segments of the polyether block amide material comprise polyethyleneoxide, i.e. a polymer of the formula $$HO-[CH_2-CH_2-O]_n-H.$$

The polyamide segments of the polyether block amide material may comprise polyamide-12, polyamide-11 or polyamide-12.12, preferably polyamide-12. The nomenclature of the polyamides corresponds to an internationally recognised system, where a number indicates the number of carbon atoms in a compound used to prepare the polyamide. If only one number is given, it means that the polyamide is derived from a aminocarboxylic acid having that number of carbon atoms. If two numbers are given, the first number indicates the number of carbon atoms of a starting diamine and the last number indicates the number of carbon atoms of a starting dicarboxylic acid.

The polyether block amide material may comprise polyether segments and polyamide segments in a ratio of polyether to polyamide of from about 60:40 to about 40:60, preferably from about 60:40 to about 50:50.

A gas sampling line having a channel for conducting respiratory gases traversing, in addition to the patient interface connector and the gas monitor connector, only the above-mentioned gas sampling tube provides, in addition to its functional performance in view of moisture and water removal as well as non-adsorption and non-absorption of gas components, further advantages: Manufacture, e.g. extrusion, of the gas sampling tube from only one starting material is considerably simpler than a process of manufacture involving joining tube portions of different materials together. Furthermore, a smooth inner surface of the channel, without material seams, may more easily be achieved by such a gas sampling line. Thus, the risk for signal distortion is decreased.

It is, however, contemplated that parts of the channel for conducting respiratory gases may traverse tube sections of other materials, such as PVC or other conventional tube materials, included in the gas sampling line, in addition to the above-mentioned gas sampling tube. Such a design is preferred when a gas sampling line having a combination of different properties, as provided by different tube materials, is desired. It may also be a cost-effective solution to combine a lower priced tube material with the gas sampling tube, particularly for long gas sampling lines.

It is advantageous when the gas sampling line further comprises a drying assembly comprising
a casing; and
a hydrophilic member disposed within the casing and being in fluid contact with the channel,
wherein the casing is comprised of a second polyether block amide material, the polyether segments of which comprise polyethyleneoxide.

Fluid contact between the hydrophilic member and the channel may be obtained, e.g., by surrounding a portion of the channel by a part of the hydrophilic member or by disposing a part of the hydrophilic member within a portion of the channel. When the gas sampling line comprises such a drying assembly, water or moisture present in respiratory gases conducted in the channel may be absorbed in, adsorbed to and/or stopped by the hydrophilic member. The hydrophilic member provides a wicking action, transporting moisture or water to the casing through which it is removed, thus not accumulating in the drying assembly. As described above in connection with the gas sampling tube, moisture and condensed water permeate through the polyether block amide material of the casing. Consequently, the drying assembly, and thus the entire gas sampling line, may be used for a prolonged period of time without change thereof.

A drying assembly as disclosed above and further detailed below may also be applied in a conventional gas sampling line, i.e. a gas sampling line wherein the gas is conducted through a tube of a conventional tube material not permeable by moisture and/or water.

The hydrophilic member may consist of a hydrophilic filter material having a large filtering area and being able to absorb moisture and water, e.g. in the form of sudden bursts of condensed water not yet removed during passage of the sampled gas through the gas sampling line. The drying assembly is typically positioned, along the gas sampling line, close to the end intended for connection to a gas monitor, e.g. adjacent to the gas monitor connector, in order to provide a final hinder to any water or moisture not removed during passage of the sampled gas through the gas sampling line.

The polyamide segments of the second polyether block amide material may comprise polyamide-12, polyamide-11 or polyamide-12.12, preferably polyamide-12. The second polyether block amide material may comprise polyether segments and polyamide segments in a ratio of polyether to polyamide of from about 60:40 to about 40:60, preferably from about 60:40 to about 50:50. Further properties and advantages of second polyether block amide material resemble those of the first polyether block amide material and may be gathered above.

The drying assembly may extend along the outside of a member defining the channel. This is an advantageous arrangement in that the hydrophilic member may transport moisture or water to a large area casing, thus allowing for efficient moisture and water permeation through the casing material, while maintaining a compact design of the gas sampling line. In particular, it is to be mentioned that the drying assembly may extend along the outside of the gas sampling tube as well as along the outside of tube sections of other materials, included in the gas sampling line. Alternatively, it may be suitable to arrange the hydrophilic member within the gas sampling tube being comprised of the polyether block amide material. A portion of the gas sampling tube being comprised of the polyether block amide material may, in other words, surround the hydrophilic member, said portion of the gas sampling tube thus representing the casing of the drying assembly.

The drying assembly may further comprise a hydrophobic member disposed across the channel. The hydrophobic member acts as a hydrophobic filter allowing the sampled gases to pass while protecting the gas monitor from undesirable substances or objects (e.g. bacteria or other bodily excretions) present in the sampled gas and hindering any remaining water from reaching the gas monitor. The hydrophobic member may or may not be positioned within the housing.

Gas sampling lines according to the invention are typically single patient use disposables. The gas sampling lines may be adapted for a wide range of patient categories, such as infant, adult, or paediatric patients. It is particularly useful to provide a gas sampling line adapted for patients having a high breath rate, such as infants, and/or a weak respiration (i.e. providing a low gas flow in the gas sampling line), such as infants and/or pediatrics. The gas sampling lines may be adapted to a wide range of applications, such as gas sampling from intubated patients, or nasal and/or oral gas sampling. Accordingly, in order to serve different patient categories or to allow use in different applications, the patient respiratory interface connector may be a nasal prong, a nasal cannula, an oral prong, a conical fitting, or a male or female Luer end. Thus, it is to be understood that the term "patient respiratory interface" may refer to an organ, e.g. the nose, of a patient as well as to a connection point in the respiratory loop of a mechanically ventilated patient. Although the gas sampling lines may be provided in any length, a typical length suited for practical use would be 1 to 3 m.

Gas samples drawn through a gas sampling line according to the invention are typically intended for analysis in a gas monitor, such as a spectroscopic analyser. The gas monitor connector of the gas sampling line is preferably designed, together with the gas monitor receptacle, to provide a smooth gas path without a dead volume, to provide a safe no-break, no-leakage connection and a to allow for a practically convenient handling of the patient, the sampling line and the gas monitor. Typical features provided by a preferred combination of the gas monitor connector of the sampling line and a gas monitor receptacle are an audible or otherwise perceptible "click" feedback assuring an operator that the gas monitor connector has correctly "clicked" into place in the gas monitor receptacle, a rotatable connection of the gas sampling line to the gas monitor, facilitating an operator's handling of the gas analysis system, absence of any intermediate connection elements, such as adapters, between the gas monitor connector and the gas monitor receptacle, thus providing a smooth gas path while avoiding risks for undesirable leakage, detection, e.g. by optical sensors, of a correct connection of the gas sampling line to the gas monitor and allowing, e.g., a sampling pump or the analyser to operate only when a correct connection is established, thereby improving the lifetime of components of the gas analysis system, and/or visual signals informing an operator of the operational status of the gas analysis system, e.g. green light when in operation, red light if occluded and blue light if an anesthetic agent is detected.

In a second aspect of the invention, there is provided use of a tube comprised of a polyether block amide material, the polyether segments of which comprise polyethyleneoxide, for sampling of respiratory gases. Discussed above are advantageous compositions of the polyether block amide material.

In a third aspect of the invention, there is provided a method for sampling of respiratory gases, the method comprising conducting respiratory gases through a tube comprised of a polyether block amide material, the polyether segments of which comprise polyethyleneoxide. Again, advantageous compositions of the polyether block amide material are discussed above.

In a fourth aspect of the invention, there is provided a gas analysis system for analysing respiratory gases, comprising a gas sampling line as defined above and a gas monitor connectable to the gas sampling line. The gas analysis system may further comprise a respiratory device, such as a respirator, connectable to the patient respiratory interface.

BRIEF DESCRIPTION OF THE DRAWING

FIG. 1 is a schematic sectional view of a portion of a gas sampling line.

DETAILED DESCRIPTION OF AN EMBODIMENT OF THE INVENTION

Referring to FIG. 1, some details of a an embodiment of a gas sampling line will be explained. The gas sampling line comprises a gas sampling tube 1, comprised of a material as specified above, connecting a patient respiratory interface connector (not shown) and a gas monitor connector 2. A gas monitor (not shown) may be coupled to the gas monitor connector 2. The gas sampling line further comprises a drying assembly comprising a housing 3, comprised of a material as specified above, and a hydrophilic member 4 disposed within the casing. The drying assembly 3, 4 extends along the outside of the gas sampling tube 1. The hydrophilic member is in fluid contact with a channel 5 for conducting respiratory gases traversing the gas sampling line. A hydrophobic member 6 is disposed across the channel 5.

When a sample of respiratory gases is conducted through the channel 5 of the gas sampling line towards the gas monitor connector 2, moisture or water present in the sample will be adsorbed to or absorbed by the hydrophilic member 4. A wicking action of the hydrophilic member 4 will transport the moisture or water towards the housing 3. Subsequently, moisture or water will permeate the housing 3 and be removed into surrounding air. The respiratory gases will pass the hydrophobic member 6 on their way towards the gas monitor connector 2, whereas undesirable objects or substances (e.g. bacteria, body excretions) will be withheld by the hydrophobic member 6 and not reach the gas monitor. The hydrophobic member 6 also serves as an additional measure to stop water or moisture from reaching the gas monitor.

It is to be understood that the invention is not to be limited to the disclosed embodiment, but on the contrary, is intended to cover various modifications and equivalent arrangements included within the spirit and scope of the appended claims.

EXAMPLES

Characteristics and advantages of the present invention are further illustrated by the following, non-limiting, examples.

Preparation of Gas Sampling Tubes According to the Invention

Gas sampling tubes according to the invention were prepared by extrusion of a polyether block amide material (available from Atofina under the trade name Pebax®) to form a tubing having an inner diameter of 1 mm and an outer diameter of 2.5 mm, and subsequent cutting of the tubing to obtain gas sampling tubes having a length of 2 m. The composition of the polyether block amide material is shown in Table 1.

TABLE 1

Gas sampling tube according to the present invention

| Tube no. | Composition |
|---|---|
| 1 | polyether block amide material of 55% polyethyleneoxide and 45% polyamide-12 |

Preparation of Comparative Gas Sampling Tubes

As comparative gas sampling tubes were used 2 m lengths of four different tubings having an inner diameter of 1 mm and an outer diameter of 2.5 mm. The composition of the tubing materials and the construction of the tubings are shown in Table 2. Comparative tubes 3-5 represent well-known embodiments of gas sampling tubes used in respiratory care for the conduction of gases to gas analysis equipment.

TABLE 2

Comparative gas sampling tubes

| Tube no. | Composition and construction |
|---|---|
| 2 | polyether block amide material of 53% polytetramethylene oxide and 47% polyamide-12 (extruded) |
| 3 | polyvinylchloride (extruded) |
| 4 | polyvinylchloride/polyethylene (co-extruded; inner layer PVC, outer layer PE) |
| 5 | polyvinylchloride + Nafion ® (1.9 m PVC joined to 0.1 m Nafion ®) |

Test Methods

All tests were performed at room temperature of about 22° C. at a gas flow of 50 ml/min through the gas sampling tube. In the tests, tube no. 5 was arranged so that in the direction of the gas flow, the Nafion® portion was upstream of the PVC portion.

A) Moisture test: A gas sample of moist air was passed from a simulated patient circuit, equipped with a heated humidifier, through a gas sampling tube to a water trap having a volume typical for disposable water traps for analysis of respiratory gases. The moist air leaving the simulated patient circuit had a relative moisture of 95-100% at 35-37° C. Water condensed in the tube was collected in the water trap and the time until the water trap had been filled with 200 µl liquid was recorded.

B) Water test: A gas sample comprising dry air and drops of water was passed from a simulated patient circuit, equipped with a syringe pump for delivery of water, through a gas sampling tube to a water trap having a volume typical for disposable water traps for analysis of respiratory gases. The syringe pump was set to deliver one droplet of water per minute, corresponding to 100 µl liquid per hour. The liquid was collected in the water trap and the time until the water trap had been filled with 200 µl liquid was recorded.

C) $CO_2$ accuracy: The sampling tube was connected between an equipment providing alternating two reference gases (5% $CO_2$ balanced $N_2$ and synthetic air) according to EN ISO 21647:2004 (Medical electrical equipment—Particular requirements for the basic safety and essential performance of respiratory gas monitors), figure 102, and a gas monitor. The measuring equipment was set to alternate the reference gases at a frequency corresponding to 40 breaths per minute. The ratio of $CO_2$ concentration measured by the gas monitor and $CO_2$ concentration of the reference gas was recorded.

D) Halothane accuracy: The sampling tube was connected between an equipment providing alternating two reference gases (5% $CO_2$, 5% halothane balanced $N_2$ and synthetic air) according to EN ISO 21647:2004, figure 102, and a gas monitor. The measuring equipment was set to alternate the reference gases at a frequency corresponding to 40 breaths per minute. The ratio of halothane concentration measured by the gas monitor and halothane concentration of the reference gas was recorded.

Results

The results are shown in Table 3. The gas sampling tube according to the invention (tube no. 1) provided an outstanding combination of desirable results in the moisture and water tests as well as in the $CO_2$ accuracy and halothane accuracy tests.

TABLE 3

| | Results | | | |
|---|---|---|---|---|
| Tube no. | A) Moisture test (h) | B) Water test (h) | C) $CO_2$ accuracy | D) Halothane accuracy |
| 1 | >24 | >24 | 0.98 | 0.98 |
| 2 | 2.5 | 2 | 0.98 | 0.98 |
| 3 | 2.5 | 2 | 0.98 | 0.73 |
| 4 | 2.5 | 2 | 0.98 | 0.98 |
| 5 | >24 | 2 | 0.97 | 0.74 |

The invention claimed is:

1. A gas sampling line having a channel for conducting respiratory gases comprising:
   a gas sampling tube surrounding a portion of the channel;
   a drying assembly extends along the outside of the gas sampling tube, wherein the drying assembly comprises:
      a casing comprised of a polyether block amide material, wherein the polyether block amide material comprises polyether segments and polyamide segments, and the polyether segments comprise polyethyleneoxide; and
      a hydrophilic member disposed within the casing and being in fluid contact with the channel, wherein the hydrophilic member is between the casing and the channel.

2. The gas sampling line according to claim 1, wherein the gas sampling tube is made by a material that is not permeable by moisture and/or water.

3. The gas sampling line according to claim 1, wherein the polyamide segments of the polyether block amide material is selected from the group consisting of polyamide-12, polyamide-11, and polyamide-12.12.

4. The gas sampling line according to claim 1, wherein the polyether segments and the polyamide segments in the polyester block amide material has a ratio from about 60:40 to about 40:60.

5. The gas sampling line according to claim 1, wherein the drying assembly further comprises a hydrophobic member disposed across the channel.

6. The gas sampling line according to claim 1, further comprising:

a patient respiratory interface connector adapted to couple the gas sampling line to a patient respiratory interface; and a gas monitor connector adapted to couple the gas sampling line to a gas monitor.

7. A method for sampling of respiratory gases, the method comprising conducting respiratory gases through the gas sampling line of claim 1.

8. The method according to claim 7, wherein the polyamide segments of the polyether block amide material is selected from the group consisting of polyamide-12, polyamide-11, and polyamide-12.12.

9. The method according to claim 7, Wherein the first polyester block amide material comprises polyether segments and polyamide segments in a ratio of polyether to polyamide from about 60:40 to about 40:60.

10. The method according to claim 7, wherein the drying assembly further comprises a hydrophobic member disposed across the channel.

11. A gas drying assembly for drying respiratory gases comprising:

a tubular casing comprised of a polyether block amide material, wherein the polyether block amide material comprises polyether segments and polyamide segments, and the polyether segments comprise polyethyleneoxide; and a hydrophilic member disposed within the casing and being in fluid communication with a channel that conduct respiratory gases, wherein the hydrophilic member is between the casing and the channel.

12. The gas drying assembly according to claim 11, wherein the polyamide segments of the polyether block amide material is selected from the group consisting of polyamide-12, polyamide-11, and polyamide-12.12.

13. The gas drying assembly according to claim 11, wherein the polyether segments and the polyamide segments in the polyester block amide material has a ratio from about 60:40 to about 40:60.

14. A gas analysis system for analysing respiratory gases, comprising a gas sampling line as defined in claim 6 and a gas monitor connectable to the gas sampling line.

15. The gas analysis system according to claim 14, further comprising a respiratory device connectable to the patient respiratory interface.

16. The gas drying assembly according to claim 13, wherein the ratio of the polyether segments to the polyamide segments is from about 60:40 to about 50:50.

17. The gas drying assembly according to claim 11, wherein the hydrophilic member contacts at least a portion of the tubular casing.

18. The gas drying assembly according to claim 11, further comprises a hydrophobic member disposed across the channel at a down-stream end of the drying assembly.

* * * * *